(12) United States Patent
Pensel

(10) Patent No.: US 6,532,108 B1
(45) Date of Patent: Mar. 11, 2003

(54) OPERATING MICROSCOPE STAND FOR X-Y DISPLACEMENT

(75) Inventor: Juergen Pensel, Altstätten (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/744,371

(22) PCT Filed: Jul. 30, 1999

(86) PCT No.: PCT/EP99/05448

§ 371 (c)(1),
(2), (4) Date: Jan. 23, 2001

(87) PCT Pub. No.: WO00/08508

PCT Pub. Date: Feb. 17, 2000

(30) Foreign Application Priority Data

Jul. 31, 1998 (CH) .............................................. 1620/98

(51) Int. Cl.⁷ ............................................... G02B 21/00
(52) U.S. Cl. ............... 359/384; 248/123.2; 248/280.11
(58) Field of Search ................................ 359/384, 382, 359/368; 248/123.11, 123.2, 280.11, 281.11, 285.1

(56) References Cited

U.S. PATENT DOCUMENTS 4,741,607 A * 5/1988 Heller ........................ 350/522
5,345,538 A * 9/1994 Narayannan et al. ...... 395/2.84
5,661,598 A     8/1997 Tomioka ..................... 359/388
5,713,545 A * 2/1998 Nakamura ................ 248/123.2
5,818,638 A * 10/1998 Nakamura ................... 359/384
6,050,530 A * 4/2000 Nakamura .................. 24/123.2

FOREIGN PATENT DOCUMENTS

| DE | 1 901 180 | 11/1969 |
| DE | 2 161 396 | 7/1972 |
| DE | 40 32 207 A1 | 4/1991 |
| DE | 43 42 717 A1 | 6/1994 |
| DE | 43 20 443 A1 | 12/1994 |
| DE | 44 16 178 A1 | 12/1994 |
| EP | 0 554 711 A1 | 8/1993 |
| EP | 0 677 278 A1 | 10/1995 |
| JP | 07 072394 | 3/1995 |

* cited by examiner

Primary Examiner—Mark A. Robinson
(74) Attorney, Agent, or Firm—Hodgson Russ LLP

(57) ABSTRACT

The invention concerns a stand for a microscope (6), having an X-Y displacement unit (5), a stand beam (3), a stand column (2), and a stand foot (1), the X-Y displacement unit (5) being no longer arranged, as before, in the region of microscope (6), but rather removed therefrom in the direction of the stand column (2). The X-Y displacement unit thus carries at least a part of the stand beam (3). The location of the center of gravity on the stand is thereby favorably influenced. Both the stand beam (3) and the stand foot (1) can be small.

19 Claims, 4 Drawing Sheets

OPERATING MICROSCOPE STAND FOR X-Y DISPLACEMENT

Many conventional stands, for example those for surgical microscopes for ophthalmology, have at their free end, between the microscope and the vertical stand support, an X-Y displacement unit for the microscope. The purpose of this displacement unit is to position the microscope in the X-Y direction in the millimeter range. This kind of arrangement of the X-Y displacement unit is generally irritating to a user, since both visibility and freedom of movement are restricted. In addition, the X-Y displacement unit considerably increases the weight on the extension arm, and usually must be compensated for by way of a corresponding counterweight or supported by a stand foot of corresponding size. As a consequence, the entire carrier arm structure of the stand beam, and optionally also the entire stand foot structure, must therefore also have greater dimensions and, in particular, a larger area.

It is therefore the object of the invention to find a stand construction in which the X-Y shifting function is retained, but any considerable weight increase in the carrier arm construction, and the further disadvantages resulting therefrom, are avoided.

In this context, the invention is not necessarily to be limited to a linear shift in two stages occurring one after the other, or to a linear displacement in general. The invention also encompasses any movements, for example calculated or controlled curved, rotary, or pivoting movements in a horizontal plane, but optionally also Z-axis shifts in a vertical plane.

The object is achieved by the relocation, according to the present invention, of the X-Y displacement unit at least closer to the vertical stand column, so that the X-Y positioning unit moves not only the microscope but also at least a portion of the horizontal stand beam.

According to the present invention, the X-Y displacement unit is not necessarily limited to carriage-like displacement tracks. It can also comprise, for example, at least two motor-driven pivot joints of the horizontal stand beam, whose mutually coordinated pivoting motions allow any desired change in the position of the microscope in an X-Y plane. The advantage of such motorized drives, with integrated incremental transducers and a corresponding control system, lies in their low weight and in a relatively more favorable cost as compared to X-Y linear displacement units.

In a preferred embodiment, the horizontal stand beam is extended, in a manner heretofore not generally common in ophthalmology microscopes, out beyond the vertical stand column and equipped there with a counterweight, so that the X-Y shifting device engages below or at least in the vicinity of the center of gravity of said extended horizontal beam.

A further improved embodiment couples the horizontal stand beam to the support for the counterweight in such a way that pivoting of the microscope results in a pivoting of the counterweight in the compensating direction for purposes of dynamic weight balancing.

The relocation of the X-Y shifting unit can also be applied independently of the pivotability of the extended horizontal beam, and vice versa.

The manner of achieving the aforesaid object is protected in the combination of features of Claim 1. It is possible by way of the invention to reduce the weight and volume on the load arm of the stand, and in that fashion to make the overall stand structure smaller. Any counterweight devices, and optionally the stand foot as well, are decreased in terms of dimensions and weight.

In addition, the need to convey electrical control lines by way of the horizontal stand carrier arm for the drive systems in the X-Y displacement unit is eliminated. The overall construction thereby becomes lighter and more compact. The invention is already satisfied to a first approximation if the X-Y displacement unit is arranged physically between the microscope and the vertical stand column. A stand beam can, for example, be of interrupted configuration, the one part being joined to the stand column and carrying the X-Y displacement unit, and other part being carried by the X-Y displacement unit.

What is preferred, however, is a configuration in which the X-Y displacement unit is arranged approximately in the axial region of the stand column. It can in this context be arranged in the region of the stand column, or can also be arranged below the stand column and support it. The latter variant has the advantage that the weight of the X-Y displacement unit is located as low down as possible; the variant with the X-Y displacement unit arranged at the top, on the other hand, has the advantage that less mass needs to be moved in the X-Y direction.

In any case, the arrangement of the X-Y displacement unit in the axial region of the stand column is advantageous, since the displacement unit itself does not need to be balanced out at that location.

The invention is not limited to stands having two-armed stand beams, i.e. having stand beams that carry the load on one arm and a counterweight on another arm. Any other stand construction is, of course, also suitable. What is essential to the invention is the location at which the X-Y displacement unit is attached.

According to an embodiment of the invention (also applicable independently) with a two-part stand beam, the two parts of the beam are pivotable with respect to one another, the pivotability being linkage-coupled. In other words, pivoting of the load in a specific direction causes the counterweight to pivot in the opposite direction, so as thereby once again to compensate for the physical shift in weight.

Since surgeons, in practical applications, prefer to have the X axis transverse to the longitudinal axis of the patient and the Y axis coaxial therewith, in one exemplary embodiment any rotation of the horizontal stand beam is performed about the axis of the displacement unit, so that its coordinate system is not affected.

In the case of a physical embodiment by way of a fixed axis in the stand column, or if the X-Y displacement unit is split into at least two pivot joints located in the horizontal stand beam arm, the corresponding displacement vectors are determined by computer, and are established automatically with computer assistance.

Further features of the invention, and variant embodiments, are described and protected in the dependent claims. Further features and patentable details are evident from the Figures and the description thereof.

The description of the Figures is overlapping. Identical reference characters denote identical components; reference characters with different indices denote components having the same functions but different physical configurations.

In the drawings, in schematic fashion:

Figure 1:
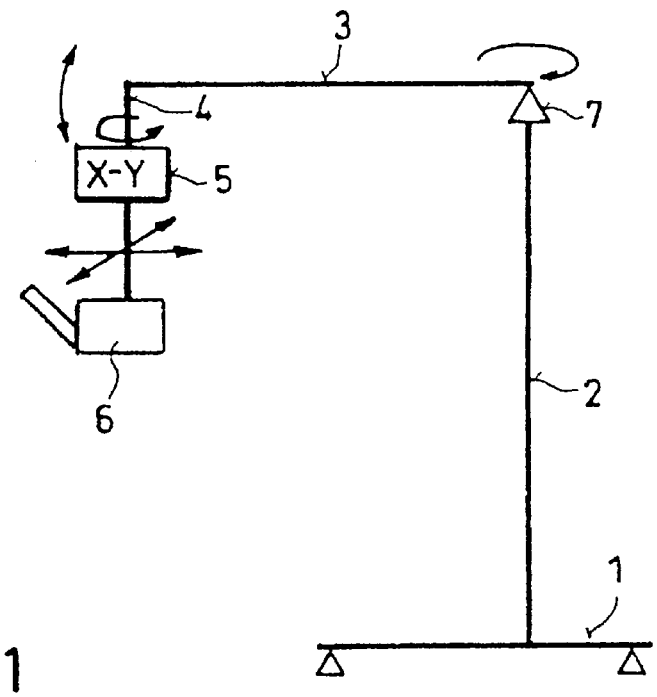
FIG. 1 shows a configuration according to the existing art, with an X-Y displacement unit directly above the microscope.
Figure 2:
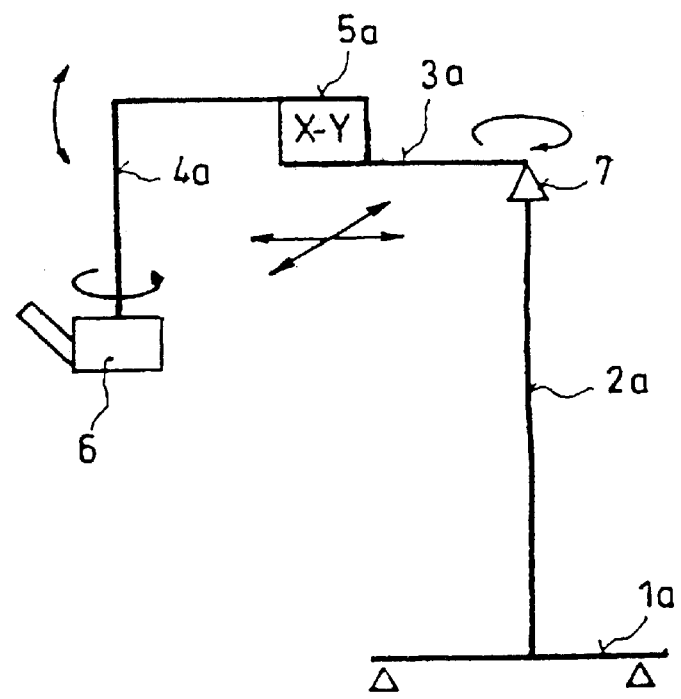
FIG. 2 shows a configuration according to the present invention, with an X-Y displacement unit arranged in offset fashion.

The first step, which is essential to the invention, lies obviously in the difference between FIGS. 1 and 2. According to the existing art, X-Y displacement unit 5 was attached directly above microscope 6 to a microscope holder 4, or divided microscope holder 4 so that its lower part was carried by X-Y displacement unit 5 and received microscope 6, while the upper part carried X-Y displacement unit 5. Any movement of the X-Y displacement unit thus brought about a shift of the two parts of microscope holder 4 with respect to one another in the X-Y direction. Microscope holder 4 was held in conventional fashion by a stand beam 3 that was held pivotably or rotatably on a pivot bearing and/or rotary bearing 7. Bearing 7 is indicated only symbolically. Any known weight compensation features, such as gas springs, cable weight compensation systems, etc. are familiar to one skilled in the art and are therefore not depicted in further detail. Bearing 7 was supported by a microscope column or stand column 2 whose bracing with respect to the floor occurs in stand foot 1. Of course there also existed in the related art stands that were braced not with respect to the floor but with respect to the ceiling, or were suspended therefrom. With these also, however, it was usual to attach the X-Y displacement unit in the region of the microscope. The present invention therefore analogously encompasses comparable mounting types.

The shifting of X-Y displacement unit 5a as shown in FIG. 2, away from microscope 6, is possible and advantageous according to the present invention both with floor-braced and with ceiling- or wall-mounted stands. The range of protection accordingly extends thereto as well. In the configuration taken as an example, as shown in FIG. 2, microscope holder 4a is once again continuous and performs the same function as a microscope holder of this kind in a microscope without an X-Y displacement unit. Stand beam 3a, however, is split in two, its part toward microscope holder 4a being carried by an X-Y displacement unit 5a, which in turn is supported on the second part of stand beam 3a. In this exemplary embodiment as in the existing art, the other end of stand beam 3a is retained on pivot bearing and/or rotary bearing 7. It is immediately evident from this that the shift of mass toward the longitudinal axis of stand column 2a causes a reduction in tilting moment. Accordingly, therefore, a stand foot 1a is already symbolically depicted as being smaller than stand foot 1 according to the existing art.

Figure 3:
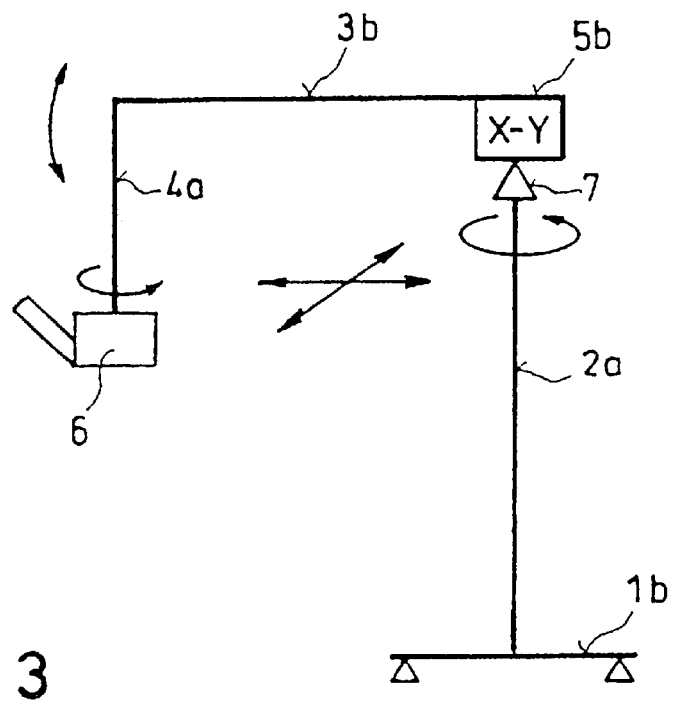
FIG. 3 shows a configuration according to the present invention, with the X-Y displacement unit in an axial stand column position.

The further development of the example shown in FIG. 3 as compared to the example shown in FIG. 2 is evident symbolically from the fact that X-Y displacement unit 5 is moved completely to the origin of a stand beam 3b, and thus supports the latter with respect to pivot bearing and/or rotary bearing 7.

Figure 4:
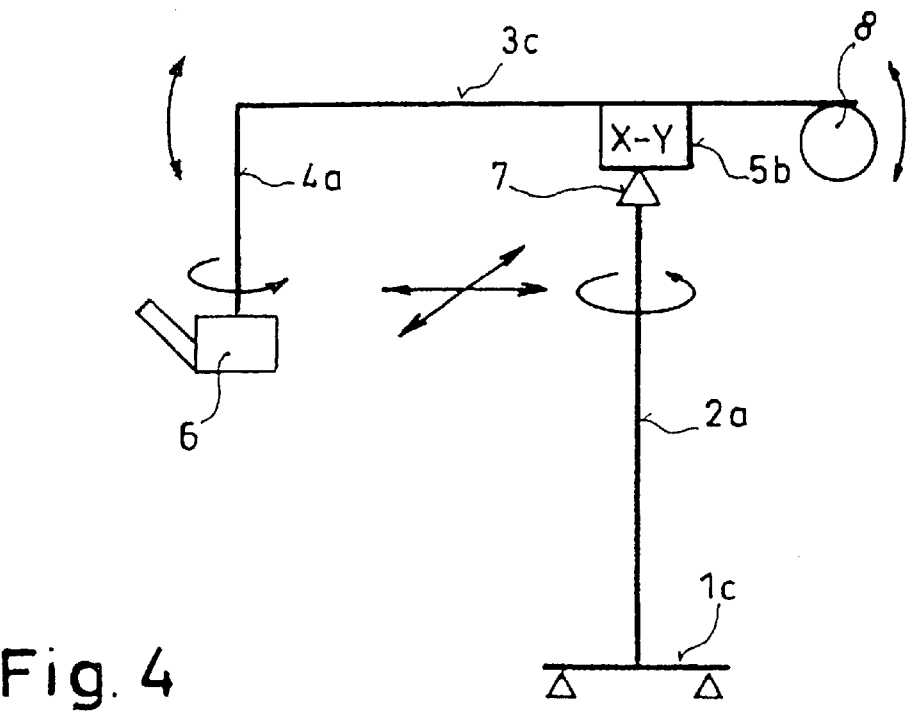
FIG. 4 shows a configuration comparable to FIG. 3, but with a two-armed stand beam.

The configuration according to the present invention shown in FIG. 4 is further developed only in that for weight compensation purposes, stand beam 3c is extended out beyond the longitudinal axis of stand column 2a so as to receive at its free end a counterweight 8. Not depicted in detail, but familiar to one skilled in the art, are features for adjusting counterweight 8 to optimize the weight compensation for microscope 6. According to the present invention, in the configurations shown in FIGS. 3, 4, and 5 it is of course advantageously no longer necessary to balance out the weight of X-Y displacement unit 5b itself.

Figure 5:
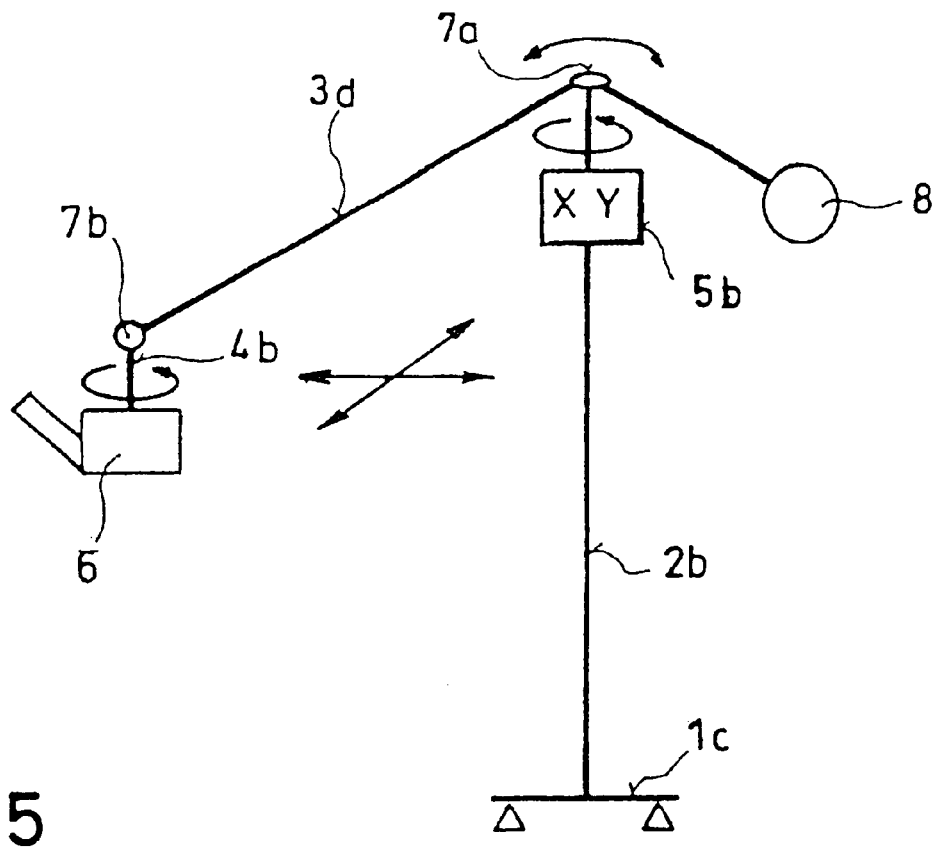
FIG. 5 shows a configuration comparable to FIG. 4, but in which the two stand beam parts are pivotable.

Further development of the configuration of FIG. 4 results in the exemplary configuration shown in FIG. 5. Here again, optimum balancing exists even with a very small stand foot 1c. In contrast to the configuration of FIG. 4, however, the two stand arm parts 3c are pivotable with respect to one another. For this purpose, they are mounted in a pivoting table and/or rotary bearing 7a that (although not depicted in detail) has a linkage or the like which causes the two parts of stand beam 3d to be pivoted, independently of one another, each in the opposite direction. The linkage or the like is configured in such a way that in the static state, i.e. when stand beam 3d is not being pivoted, it transmits the load compensation moments from microscope 6 to counterweight 8. The pivotability of the stand beam parts with respect to one another makes it possible to keep the overall center of gravity of the stand generally low down, since as a rule both the microscope and the counterweight are located below the highest point of stand column 2.

For better mobility of microscope 6 there is provided therein, between microscope holder 4b and stand beam 3d, a further pivot bearing and/or rotary bearing 7b that can by all means also be provided in the case of the other configurations in the Figures described earlier.

In the configuration as shown in FIG. 5, in contrast to the configuration according to FIG. 2 it is not stand beam 3 but stand column 2b that is interrupted in order to receive X-Y displacement unit 5b. The location of this interruption is selected optimally in terms of design features. Since the displacement travel lengths in the X-Y direction generally change, in an X-Y displacement unit, only within a range of millimeters, the displacement in the region of stand column 2 is harmless and does not cause disruptive tilting torques.

Referring to the previously mentioned interchangeability of the invention in terms of floor- or ceiling-braced or wall-mounted stands, the terms "column" and "foot" are also to be understood as "suspension beam" and "base." With a ceiling-mounted configuration of this kind, the microscope holder and the microscope would of course be arranged on the other side of stand beam 3 from that depicted in the Figures.

Figure 6:
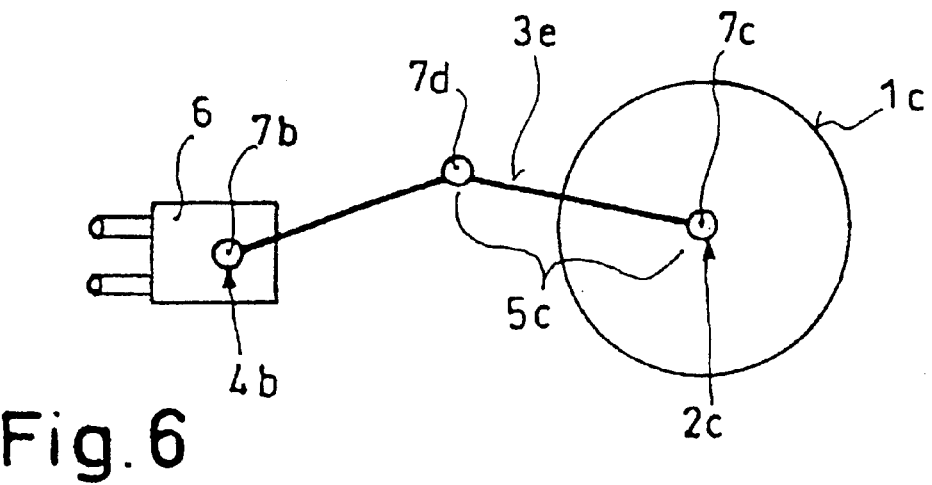
FIG. 6 shows a variant having motor-drivable pivot joints for X-Y adjustment, in plan view.

The configuration shown in FIG. 6 uses, instead of a conventional carriage-like X-Y displacement unit, a novel one 5c having two motor-drivable pivot joints 7c, d that also allow positioning of the microscope in the X-Y plane. Combinations of pivoting joins and linear displacement guides are of course also within the context of the invention.

Figure 7:
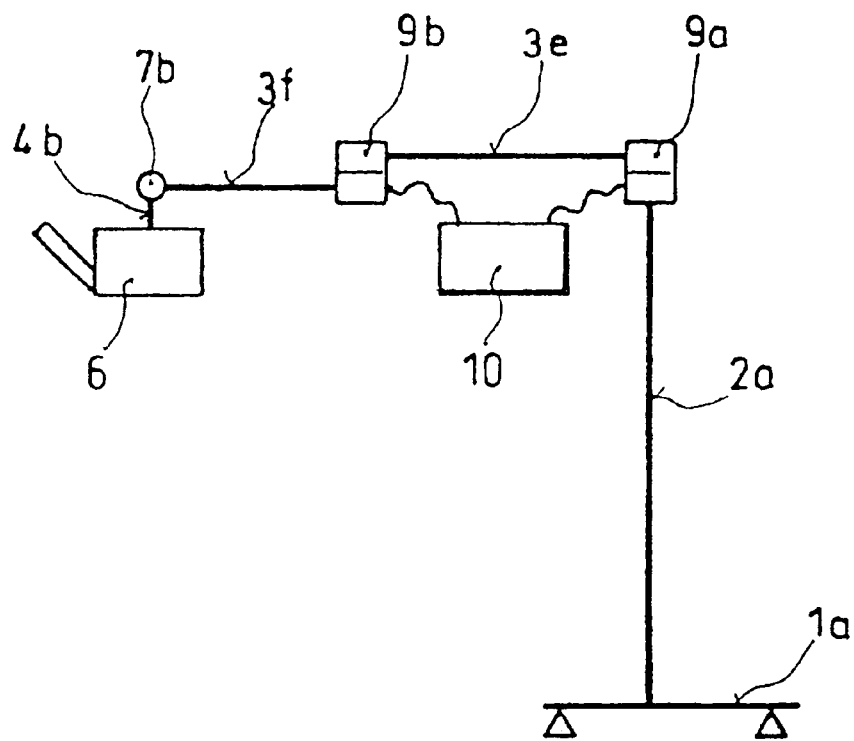
FIG. 7 shows a configuration comparable to FIG. 6, with motors and incremental transducers.
Figure 8:
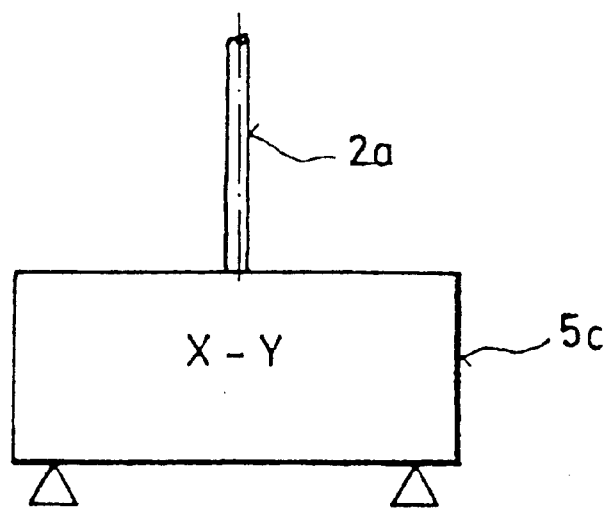
FIG. 8 shows a configuration in which the X-Y displacement unit is integrated in or below the stand foot.

The configuration shown in FIG. 7 corresponds approximately to that of FIG. 6; motors 9a and 9b, with incremental transducers, that are displaced in coordinated fashion via a control system 10 in order to achieve desired (optionally approximate) X-Y displacements, are depicted here.

Preferably all the X-Y displacement units depicted can also be decoupled, so that X-Y shifts can also be made manually.

A computer (not depicted in detail) serves, in combination with suitable sensor elements, to sense the current position of the microscope with respect to the specimen or a patient, and to recalculate the X-Y command values in each case so that the displacement motion executed is performed, for example, in the X-Y coordinate system of the specimen or patient, or in the coordinate system of the microscope, regardless of the three-dimensional pivot position of the microscope.

Parts List

| | FIG. 1 | FIG. 2 | FIG. 3 | FIG. 4 | FIG. 5 | FIG. 6 |
|---|---|---|---|---|---|---|
| 1 | Stand foot | a | b | c | c | c |
| 2 | Stand column | a | a | a | b | c |
| 3 | Stand beam or carrier arm | a | b | c | d | e |
| 4 | Microscope holder | a | a | a | b | b |
| 5 | X-Y displacement unit | a | b | b | b | c |
| 6 | Microscope | | | | | |
| 7 | Pivot bearing or rotary bearing; linkages; pivot joints | | | | a, b | c, d |
| 8 | Counterweight | | | | | |

What is claimed is:

1. A surgical microscope stand comprising:
   a stand foot;
   a stand column extending vertically from said stand foot and having a longitudinal axis;
   a stand beam supported by said stand column, said stand beam including a first portion on one side of said longitudinal axis of said stand column for carrying a surgical microscope and a second portion on an opposite side of said longitudinal axis of said stand column for carrying a counterweight; and
   an X-Y displacement unit arranged between said stand column and said stand beam, said X-Y displacement unit including X-axis and Y-axis linear shifting means for moving said stand beam relative to said stand column in a horizontal X-Y plane.

2. The stand as defined in claim 1, wherein said X-Y displacement unit further includes means for pivoting said stand beam about said longitudinal axis of said stand column.

3. The stand as defined in claim 1 wherein said X-axis and Y-axis linear shifting means includes a pair of electric motors having integrated incremental transducers.

4. The stand as defined in claim 1 wherein said stand beam is divided between said first portion and said second portion, and both said first portion and said second portion are pivotable and lockable with respect to the other portion in vertical planes.

5. The stand as defined in claim 4, wherein said first and second portions of said stand beam are interconnected by a linkage enabling independent pivoting of said first and second portions.

6. The stand as defined in claim 5 wherein said linkage includes a brake for immobilizing said first and second portions with respect to one another.

7. The stand as defined in claim 6, wherein said brake is electronically controlled.

8. The stand as defined in claim 1, wherein said stand beam is mounted above the head of a user.

9. The stand as defined in claim 1, wherein said X-Y displacement unit is mounted above the head of a user.

10. The stand as defined in claim 1, wherein said X-Y displacement unit further includes a motor-drivable pivot linkage dividing said first portion into two parts, whereby said two parts of said first portion are pivotable relative to one another in an X-Y plane.

11. The stand as defined in claim 1, wherein said X-Y displacement unit further includes a Z-axis linear shifting means for moving said stand beam relative to said stand column.

12. The stand as defined in claim 1 wherein said X-Y displacement unit further includes a Z-axis shifting means for moving said stand beam perpendicular to the X-Y plane relative to said stand column.

13. The stand as defined in claim 1 wherein said stand foot is a ceiling mount.

14. The stand as defined in claim 1 wherein said stand foot is a wall mount.

15. A surgical microscope stand comprising:
   a stand foot;
   a stand column extending vertically from said stand foot and having a longitudinal axis;
   a stand beam pivotally connected to said stand column for rotation about said longitudinal axis;
   an X-Y displacement unit receiving at least a portion of said stand beam, said X-Y displacement unit including X-axis and Y-axis linear shifting means for moving said portion of said stand beam in X and Y directions and computer control means for sending movement commands to said linear shifting means;
   a microscope holder mounted on said movable portion of said stand beam, said microscope holder enabling pivotal motion of a microscope held thereby about a vertical microscope axis; and
   sensor elements for detecting pivotal position of said microscope about said microscope axis and pivotal position of said stand beam about said longitudinal axis and providing signals indicative of said pivotal positions, said computer control means being connected to said sensor elements to receive said signals;
   said computer control means being programmed to recalculate said movement commands based on said signals;
   whereby the orientation of said X and Y directions does not change for a user with respect to an observed patient or specimen.

16. The stand as defined in claim 15, wherein said computer control means has a reset function for returning said stand to an initial calibration position relative to said patient or specimen.

17. The stand as defined in claim 15 wherein said X-Y displacement unit further includes a Z-axis shifting means for moving said portion of said stand beam perpendicular to the X-Y plane.

18. The stand as defined in claim 15 wherein said stand foot is a ceiling mount.

19. The stand as defined in claim 15, wherein said stand foot is a wall mount.

* * * * *